United States Patent
Ma et al.

(10) Patent No.: US 8,669,536 B2
(45) Date of Patent: Mar. 11, 2014

(54) METHODS AND SYSTEMS FOR IDENTIFYING INK

(71) Applicant: Hewlett-Packard Developement Company, L.P., Fort Collins, CO (US)

(72) Inventors: Zeying Ma, San Diego, CA (US); Gary William Larson, San Diego, CA (US); Lufei Lin, San Diego, CA (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 0 days.

(21) Appl. No.: 13/765,131

(22) Filed: Feb. 12, 2013

(65) Prior Publication Data

US 2013/0221277 A1    Aug. 29, 2013

Related U.S. Application Data

(63) Continuation of application No. 11/269,041, filed on Nov. 8, 2005, now abandoned.

(51) Int. Cl.
*G01N 21/64* (2006.01)
*C09D 11/00* (2006.01)

(52) U.S. Cl.
USPC ....... 250/458.1; 347/19; 106/31.14; 428/32.6

(58) Field of Classification Search
USPC ....... 250/458.1; 106/31.14; 428/32.6; 347/19
See application file for complete search history.

(56) References Cited

U.S. PATENT DOCUMENTS

| | | | |
|---|---|---|---|
| 4,363,965 A | 12/1982 | Soberman et al. | |
| 5,208,630 A | 5/1993 | Goodbrand et al. | |
| 5,474,937 A | 12/1995 | Anderson, II et al. | |
| 5,569,317 A | 10/1996 | Sarada et al. | |
| 5,660,111 A | 8/1997 | Herbert | |
| 5,760,394 A | 6/1998 | Welle | |
| 5,776,713 A | 7/1998 | Garner et al. | |
| 5,837,042 A | 11/1998 | Lent et al. | |
| 5,849,590 A | 12/1998 | Anderson, II et al. | |
| 5,942,444 A * | 8/1999 | Rittenburg et al. | 436/518 |
| 6,025,200 A | 2/2000 | Kaish et al. | |
| 6,030,657 A | 2/2000 | Butland et al. | |
| 6,138,913 A | 10/2000 | Cyr et al. | |
| 6,149,719 A * | 11/2000 | Houle | 106/31.14 |
| 6,174,400 B1 * | 1/2001 | Krutak et al. | 428/32.6 |
| 6,212,504 B1 | 4/2001 | Hayosh | |
| 6,322,182 B1 | 11/2001 | Lin et al. | |
| 6,354,501 B1 | 3/2002 | Outwater et al. | |
| 6,378,976 B1 * | 4/2002 | Byers et al. | 347/19 |
| 6,456,729 B1 | 9/2002 | Moore | |
| 6,491,215 B1 | 12/2002 | Irwin, Jr. et al. | |
| 6,501,825 B2 | 12/2002 | Kaiser et al. | |
| 6,513,921 B1 | 2/2003 | Houle | |

(Continued)

FOREIGN PATENT DOCUMENTS

| | | |
|---|---|---|
| CN | 1060098 | 4/1992 |
| CN | 1082579 | 2/1994 |

(Continued)

*Primary Examiner* — Casey Bryant

(57) ABSTRACT

An ink composition includes a colorant visible under visible light and a tagging composition, including a carrier and a detectable marker dispersed or dissolved in the carrier. The detectable marker is an isotope of an element, the isotope being present in the ink composition in a concentration ranging from about 1 parts per billion (ppb) to about 1000 ppb.

5 Claims, 7 Drawing Sheets

| | 10 ppb $^6$Li Tagged Ink Authentic | | | 5 ppb $^6$Li Ink 50% Adulterated | | | $^6$Li Counts Diluted/ Authentic | Indication | $^6$Li/$^7$Li Ratios Diluted/ Authentic | Indication |
|---|---|---|---|---|---|---|---|---|---|---|
| | $^6$Li Count | $^7$Li Count | $^6$Li/$^7$Li | $^6$Li Count | $^7$Li Count | $^6$Li/$^7$Li | | | | |
| A2 | 6,394 | 1,770 | 3.61 | 2,659 | 831 | 3.20 | 0.42 | Fake 1 | 0.89 | Authentic |
| B2 | 46,878 | 3,915 | 11.97 | 23,203 | 3,708 | 6.26 | 0.49 | Fake 1 | 0.52 | Fake 2 |
| C2 | 32,665 | 21,824 | 1.50 | 24,992 | 17,132 | 1.46 | 0.77 | Authentic | 0.97 | Authentic |
| D2 | 20,897 | 4,508 | 4.64 | 11,910 | 3,060 | 3.89 | 0.57 | Fake 1 | 0.84 | Authentic |
| E2 | 16,079 | 7,177 | 2.24 | 11,493 | 8,192 | 1.40 | 0.71 | Authentic | 0.63 | Fake 2 |

(56) References Cited

U.S. PATENT DOCUMENTS

| | | |
|---|---|---|
| 6,743,283 B2 | 6/2004 | Imanishi et al. |
| 6,750,756 B2 | 6/2004 | Stevenson et al. |
| 6,793,723 B2 | 9/2004 | Auslander et al. |
| 6,846,350 B2 | 1/2005 | Imanishi et al. |
| 6,861,012 B2 | 3/2005 | Gardner et al. |
| 2001/0035902 A1 | 11/2001 | Iddan et al. |
| 2003/0018120 A1 | 1/2003 | Lee et al. |
| 2004/0184660 A1 | 9/2004 | Treado et al. |
| 2004/0220298 A1 | 11/2004 | Kozee et al. |
| 2006/0044332 A1 | 3/2006 | Auslander et al. |
| 2009/0226835 A1* | 9/2009 | Mayo et al. ............ 430/108.21 |

FOREIGN PATENT DOCUMENTS

| | | |
|---|---|---|
| GB | 1233001 | 5/1971 |
| JP | 2002226740 | 8/2002 |
| JP | 2002317138 | 10/2002 |
| WO | WO-99/00666 | 1/1999 |
| WO | WO-01/40795 | 6/2001 |
| WO | WO-02/068945 | 9/2002 |

* cited by examiner

FIG. 1

| | 10 ppb 6Li Tagged Ink Authentic | | | 8 ppb 6Li Ink 20% Adulterated | | | 6Li Counts Adulterated/ Authentic | Indication | 6Li/7Li Ratios Adulterated/ Authentic | Indication |
|---|---|---|---|---|---|---|---|---|---|---|
| | 6Li Count | 7Li Count | 6Li/7Li | 6Li Count | 7Li Count | 6Li/7Li | | | | |
| A1 | 12,583 | 2,828 | 4.45 | 10,083 | 4,196 | 2.40 | 0.80 | Authentic | 0.54 | Fake 2 |
| A2 | 6,394 | 1,770 | 3.61 | 5,440 | 4,648 | 1.17 | 0.85 | Authentic | 0.32 | Fake 2 |
| B1 | 13,039 | 950 | 13.73 | 10,007 | 2,622 | 3.82 | 0.77 | Authentic | 0.28 | Fake 2 |
| B2 | 46,878 | 3,915 | 11.97 | 42,701 | 67,412 | 0.63 | 0.91 | Authentic | 0.05 | Fake 2 |
| C1 | 23,476 | 14,806 | 1.59 | 14,655 | 12,085 | 1.21 | 0.62 | Fake1 | 0.76 | Authentic |
| C2 | 32,665 | 21,824 | 1.50 | 30,384 | 57,715 | 0.53 | 0.93 | Authentic | 0.35 | Fake 2 |
| D1 | 34,800 | 7,496 | 4.64 | 27,519 | 12,317 | 2.23 | 0.79 | Authentic | 0.48 | Fake 2 |
| D2 | 20,897 | 4,508 | 4.64 | 19,166 | 27,739 | 0.69 | 0.92 | Authentic | 0.15 | Fake 2 |
| E1 | 27,319 | 11,671 | 2.34 | 23,079 | 21,503 | 1.07 | 0.84 | Authentic | 0.46 | Fake 2 |
| E2 | 16,079 | 7,177 | 2.24 | 14,157 | 21,367 | 0.66 | 0.88 | Authentic | 0.30 | Fake 2 |

FIG. 2

| | 10 ppb 6Li Tagged Ink Authentic | | | 5 ppb 6Li Ink 50% Adulterated | | | 6Li Counts Adulterated/ Authentic | Indication | 6Li/7Li Ratios Adulterated/ Authentic | Indication |
|---|---|---|---|---|---|---|---|---|---|---|
| | 6Li Count | 7Li Count | 6Li/7Li | 6Li Count | 7Li Count | 6Li/7Li | | | | |
| A1 | 12,583 | 2,828 | 4.45 | 6,100 | 4,018 | 1.52 | 0.48 | Fake 1 | 0.34 | Fake 2 |
| A2 | 6,394 | 1,770 | 3.61 | 3,461 | 4,117 | 0.84 | 0.54 | Fake 1 | 0.23 | Fake 2 |
| B1 | 13,039 | 950 | 13.73 | 6,351 | 2,860 | 2.22 | 0.49 | Fake 1 | 0.16 | Fake 2 |
| B2 | 46,878 | 3,915 | 11.97 | 22,998 | 33,409 | 0.69 | 0.49 | Fake 1 | 0.06 | Fake 2 |
| C1 | 23,476 | 14,806 | 1.59 | 9,166 | 11,705 | 0.78 | 0.62 | Fake 1 | 0.49 | Fake 2 |
| C2 | 32,665 | 21,824 | 1.50 | 19,592 | 44,435 | 0.44 | 0.60 | Fake 1 | 0.29 | Fake 2 |
| D1 | 34,800 | 7,496 | 4.64 | 15,859 | 10,103 | 1.57 | 0.46 | Fake 1 | 0.34 | Fake 2 |
| D2 | 20,897 | 4,508 | 4.64 | 11,878 | 17,737 | 0.67 | 0.57 | Fake 1 | 0.14 | Fake 2 |
| E1 | 27,319 | 11,671 | 2.34 | 15,811 | 22,210 | 0.71 | 0.58 | Fake 1 | 0.14 | Fake 2 |
| E2 | 16,079 | 7,177 | 2.24 | 9,504 | 17,416 | 0.55 | 0.59 | Fake 1 | 0.24 | Fake 2 |

| | 10 ppb ⁶Li Tagged Ink Authentic | | | 2 ppb ⁶Li Ink 80% Adulterated | | | ⁶Li Counts Adulterated/ Authentic | Indication | ⁶Li/⁷Li Ratios Adulterated/ Authentic | Indication |
|---|---|---|---|---|---|---|---|---|---|---|
| | ⁶Li Count | ⁷Li Count | ⁶Li/⁷Li | ⁶Li Count | ⁷Li Count | ⁶Li/⁷Li | | | | |
| A1 | 12,583 | 2,828 | 4.45 | 2,605 | 3,649 | 0.71 | 0.21 | Fake 1 | 0.16 | Fake 2 |
| A2 | 6,394 | 1,770 | 3.61 | 1,500 | 3,879 | 0.39 | 0.23 | Fake 1 | 0.11 | Fake 2 |
| B1 | 13,039 | 950 | 13.73 | 3,339 | 5,044 | 0.66 | 0.26 | Fake 1 | 0.05 | Fake 2 |
| B2 | 46,878 | 3,915 | 11.97 | 13,929 | 71,256 | 0.20 | 0.30 | Fake 1 | 0.02 | Fake 2 |
| C1 | 23,476 | 14,806 | 1.59 | 3,604 | 9,693 | 0.37 | 0.15 | Fake 1 | 0.23 | Fake 2 |
| C2 | 32,665 | 21,824 | 1.50 | 10,929 | 58,239 | 0.19 | 0.33 | Fake 1 | 0.13 | Fake 2 |
| D1 | 34,800 | 7,496 | 4.64 | 6,254 | 8,050 | 0.78 | 0.18 | Fake 1 | 0.17 | Fake 2 |
| D2 | 20,897 | 4,508 | 4.64 | 6,389 | 25,890 | 0.25 | 0.31 | Fake 1 | 0.05 | Fake 2 |
| E1 | 27,319 | 11,671 | 2.34 | 7,229 | 24,899 | 0.29 | 0.26 | Fake 1 | 0.12 | Fake 2 |
| E2 | 16,079 | 7,177 | 2.24 | 4,932 | 22,750 | 0.22 | 0.31 | Fake 1 | 0.10 | Fake 2 |

FIG. 3

| | 10 ppb ⁶Li Tagged Ink Authentic | | | 5 ppb ⁶Li Ink 50% Adulterated | | | ⁶Li Counts Diluted/ Authentic | Indication | ⁶Li/⁷Li Ratios Diluted/ Authentic | Indication |
|---|---|---|---|---|---|---|---|---|---|---|
| | ⁶Li Count | ⁷Li Count | ⁶Li/⁷Li | ⁶Li Count | ⁷Li Count | ⁶Li/⁷Li | | | | |
| A2 | 6,394 | 1,770 | 3.61 | 2,659 | 831 | 3.20 | 0.42 | Fake 1 | 0.89 | Authentic |
| B2 | 46,878 | 3,915 | 11.97 | 23,203 | 3,708 | 6.26 | 0.49 | Fake 1 | 0.52 | Fake 2 |
| C2 | 32,665 | 21,824 | 1.50 | 24,992 | 17,132 | 1.46 | 0.77 | Authentic | 0.97 | Authentic |
| D2 | 20,897 | 4,508 | 4.64 | 11,910 | 3,060 | 3.89 | 0.57 | Fake 1 | 0.84 | Authentic |
| E2 | 16,079 | 7,177 | 2.24 | 11,493 | 8,192 | 1.40 | 0.71 | Authentic | 0.63 | Fake 2 |

FIG. 4

| | 10 ppb ⁶Li Tagged Ink Authentic | | | 2 ppb ⁶Li Ink 80% Adulterated | | | ⁶Li Counts Diluted/ Authentic | Indication | ⁶Li/⁷Li Ratios Diluted/ Authentic | Indication |
|---|---|---|---|---|---|---|---|---|---|---|
| | ⁶Li Count | ⁷Li Count | ⁶Li/⁷Li | ⁶Li Count | ⁷Li Count | ⁶Li/⁷Li | | | | |
| A2 | 6,394 | 1,770 | 3.61 | 802 | 312 | 2.57 | 0.13 | Fake 1 | 0.71 | Authentic |
| B2 | 46,878 | 3,915 | 11.97 | 10,761 | 1,925 | 5.59 | 0.23 | Fake 1 | 0.47 | Fake 2 |
| C2 | 32,665 | 21,824 | 1.50 | 13,558 | 10,018 | 1.35 | 0.42 | Authentic | 0.90 | Authentic |
| D2 | 20,897 | 4,508 | 4.64 | 4,432 | 2,202 | 2.01 | 0.21 | Fake 1 | 0.43 | Authentic |
| E2 | 16,079 | 7,177 | 2.24 | 6,003 | 11,977 | 0.50 | 0.37 | Authentic | 0.22 | Fake 2 |

FIG. 5

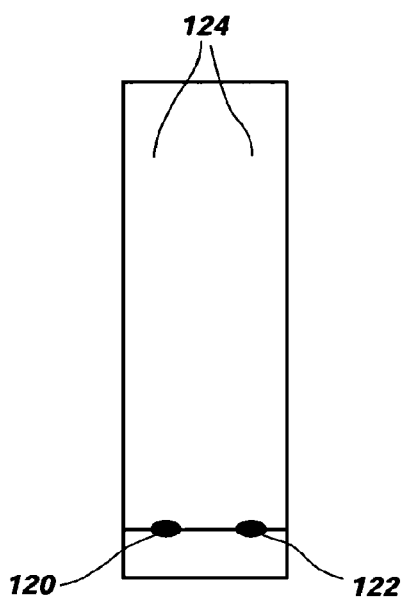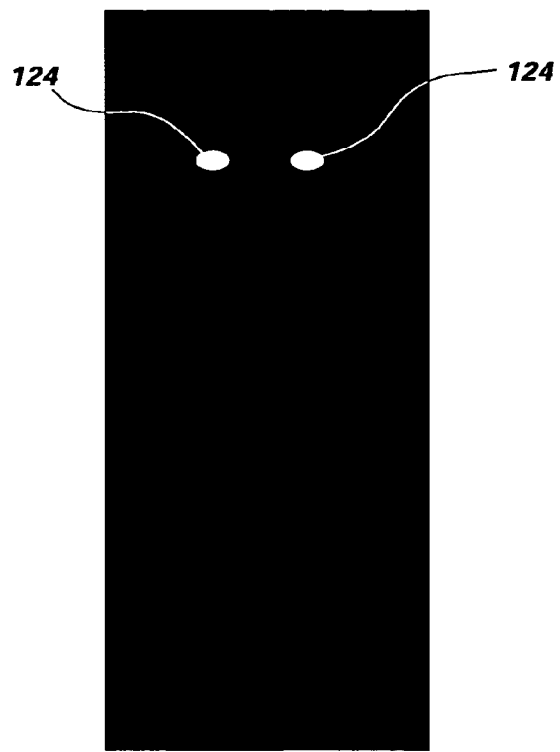
*FIG. 9A*  *FIG. 9B*

METHODS AND SYSTEMS FOR IDENTIFYING INK

CROSS REFERENCE TO RELATED APPLICATIONS

This application is a continuation of co-pending U.S. patent application Ser. No. 11/269,041, filed on Nov. 8, 2005, which is related to a patent application entitled, "Methods for Tagging and Authenticating Inks Using Compositions", U.S. patent application Ser. No. 11/269,093, also filed on Nov. 8, 2005 (now abandoned).

FIELD OF THE INVENTION

The present invention relates to methods for identifying inks. More particularly, the present invention relates to methods for tagging or adding a detectable marker to an ink. Further, the present invention relates to methods for authenticating ink samples by probing the ink for the presence of the detectable marker in an ink sample.

BACKGROUND OF THE INVENTION

Inkjet printers operate by placing small droplets of ink onto a medium, (e.g., a sheet of paper) to create an image. Inks used in inkjet printers are typically stored in and dispensed from one or more inkjet cartridges that are specific for the inkjet printer with which they are used. Once the ink in the inkjet cartridge has been used, the cartridge must be replaced or refilled. Refilling of inkjet cartridges is a relatively simple task and refill kits are readily available.

The ease with which inkjet cartridges may be refilled lends itself to a high susceptibility for counterfeiting. This can lead, for instance, to damage to the reputation of an ink manufacturer if in an inkjet cartridge is replaced with a counterfeit ink of inferior quality and sold with the manufacturer's label attached to the cartridge. Additionally, counterfeiting may lead to large expenditures of warranty monies paid out by an ink manufacturer if, for example, an authentic ink of the ink manufacturer is replaced with a counterfeit ink, or diluted, and then returned to the manufacturer accompanied by a complaint of substandard ink quality.

Techniques have been developed for tagging various articles to prevent counterfeiting or at least reduce the incidence thereof. For instance, the various articles may be tagged with code-bearing micro-particles, bulk chemical substances, or radioactive substances. However, tagging techniques that are applicable to other articles or materials are not necessarily suitable for tagging inks. Inks are typically formulated to provide maximum performance in terms of, among other traits, color, physical and chemical properties, and interaction of the ink with the medium on which they are printed.

Some identification techniques for tagging and tracing materials such as inks, paintings, explosives, pollutants, and other articles exist. These techniques may employ inorganic salts, ultraviolet (UV) absorbers, nucleic acids or metals as a tag, wherein the tag is used to identify or authenticate the tagged material. Analytical tools used to detect these tags or traces include paper chromatography, UV-visible spectrophotometers, X-ray microanalysis or electrophoresis.

Although these techniques may enable the detection or quantification of the tagged material, the incorporation of the tag into the ink may hinder ink development by the ink manufacturer. For instance, ensuring printer performance is an expensive and time-consuming process for the ink manufacturer and the prevention of counterfeiting inks further frustrates the goal of ensuring printer performance.

While some metal and other multi-valent salts may have utility in tagging certain articles, they are not suitable for tagging inks used in thermal ink-jet printers because trace amounts of unwanted cations such as $Fe^{3+}$, $Cr^{3+}$ and $Si^{4+}$ may cause mis-directed ink drops or mis-firing of the ink jet nozzles. Further, the use of UV absorbent materials or other fluorescent brighteners may add unwanted effects to color appearances of the ink or may fade upon prolonged exposure to light.

BRIEF SUMMARY OF THE INVENTION

In one embodiment, a method for identifying an ink comprises obtaining a sample of the unidentified ink and subjecting the sample of the unidentified ink to infrared light capable of causing a detectable marker, if present, in the sample of the unidentified ink to fluoresce. The method further includes determining whether fluorescence emitted from the sample of the unidentified ink, if any, corresponds to fluorescence of an authentic ink known to include the detectable marker.

In an additional embodiment, a method for tagging an ink includes providing an ink comprising a colorant visible under visible light. The method further includes mixing the ink with a detectable marker capable of fluorescing when subjected to infrared light, such that the detectable marker is present in the ink at a concentration of between about 10 ppm and about 10000 ppm.

In another embodiment, a method for deterring the incidence of ink counterfeiting is described. The method includes adding a detectable marker capable of fluorescing when subjected to infrared light or a tagging composition having at least one isotope of an element to an ink, thus producing an authentic ink. The method further includes obtaining an ink sample, exposing at least part of the ink sample to infrared light or determining whether the unidentified ink includes an abundance of at least one isotope, and determining whether the ink sample includes the detectable marker.

An ink composition is disclosed in yet another embodiment. The ink composition includes a colorant visible under visible light and means for fluorescing the same when subjected to infrared light, wherein the means for fluorescing is present in the ink composition at a concentration of between about 10 ppm and about 10000 ppm.

In yet a further embodiment, a system for identifying an unidentified ink includes a separation means for separating a detectable marker, if present, from a component of the unidentified ink. The system also includes a light source for producing infrared light and an infrared viewer for detecting fluorescence generated by the detectable marker, if present, when subjected to the infrared light.

BRIEF DESCRIPTION OF THE DRAWINGS

While the specification concludes with claims particularly pointing out and distinctly claiming that which is regarded as the present invention, the advantages of this invention may be more readily ascertained from the following description of the invention when read in conjunction with the accompanying drawings in which:

FIG. 1 is chart which illustrates the $^6Li$ isotope count, $^7Li$ isotope count, and $^6Li/^7Li$ isotope ratio of a number of authentic ink samples tagged with one embodiment of a detectable marker including 10 ppb $^6Li$ isotope and a corresponding number of ink samples which have been adulterated by 20% so that they contain 8 ppb $^6Li$;

FIG. 2 is chart which illustrates the $^6$Li isotope count, $^7$Li isotope count, and $^6$Li/$^7$Li isotope ratio of a number of authentic ink samples tagged with one embodiment of a detectable marker 10 ppb $^6$Li isotope and a corresponding number of ink samples which, in one embodiment, have been adulterated by 50% so that they contain 5 ppb $^6$Li;

FIG. 3 is chart which illustrates the $^6$Li isotope count, $^7$Li isotope count, and $^6$Li/$^7$Li isotope ratio of a number of authentic ink samples tagged with one embodiment of a detectable marker 10 ppb $^6$Li isotope and a corresponding number of ink samples which, in one embodiment, have been adulterated by 80% so that they contain 2 ppb $^6$Li;

FIG. 4 is chart which illustrates the $^6$Li isotope count, $^7$Li isotope count, and $^6$Li/$^7$Li isotope ratio of a number of authentic ink samples tagged with one embodiment of a detectable marker 10 ppb $^6$Li isotope and a corresponding number of ink samples which, in one embodiment, have been diluted by 50% so that they contain 5 ppb $^6$Li;

FIG. 5 is chart which illustrates the $^6$Li isotope count, $^7$Li isotope count, and $^6$Li/$^7$Li isotope ratio of a number of authentic ink samples tagged with one embodiment of a detectable marker 10 ppb $^6$Li isotope and a corresponding number of ink samples which, in one embodiment, have been diluted by 80% so that they contain 2 ppb $^6$Li;

FIGS. 9A and 9B illustrate results of another embodiment of a method of separating ink components from the infrared marker of the present invention viewed under visible light (FIG. 9A) and infrared lights (FIG. 9B).

DETAILED DESCRIPTION OF THE INVENTION

Figure 6:
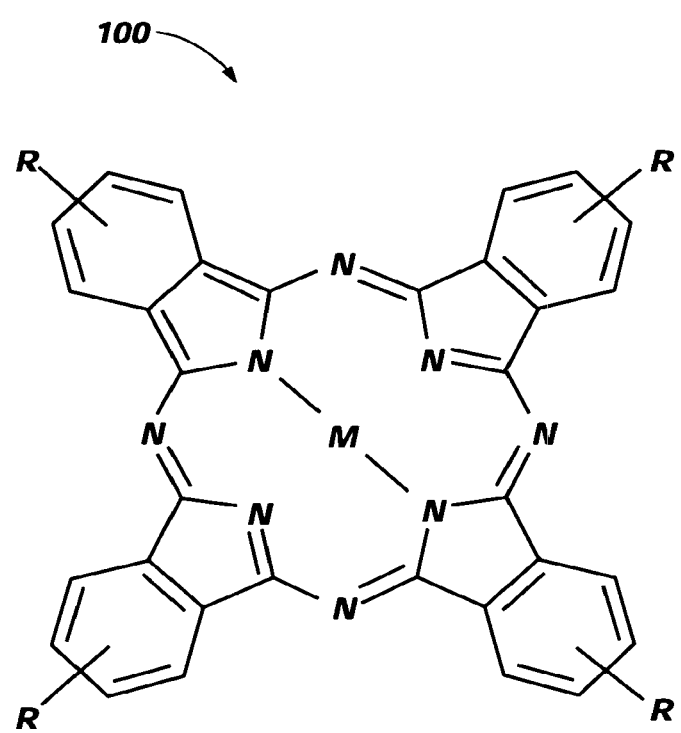
FIG. 6 is a molecular diagram of one embodiment of an infrared marker of the present invention.

The present invention is directed to methods for tagging inks with a detectable marker and methods for authenticating inks or detecting counterfeit inks. In one embodiment, the detectable marker includes at least one isotope of an element and, in another embodiment, the detectable marker comprises an infrared fluorescing agent. In other embodiments, methods for reducing the incidence of ink counterfeiting and systems for identifying an unidentified ink are described.

In one embodiment, tagging compositions are used for tagging or labeling an ink for identification and authentication. As used herein, the term "tagging composition" or "labeling composition" refers to a composition having a detectable marker. That is, the inks of the present invention are tagged or labeled with a detectable marker such that the ink comprises a detectable marker that may be used to identify or authenticate the ink. As used herein, "detectably different" abundances means that the difference between the abundance of the tagging composition prior to incorporation of the detectable marker and a respective abundance after incorporation of the detectable marker is larger than the experimental error of the detection method utilized (e.g., inductively coupled plasma mass spectrometry (ICP-MS) in the case of isotopes). The tagging compositions which may be used in the methods of the present invention may be non-toxic and inert at the desired concentration levels and are capable of incorporation into an ink without altering the attractiveness or performance thereof.

The tagging compositions of the present invention may also include a suitable carrier. The carriers are materials in which one or more detectable markers may be dispersed or dissolved. The carrier may be any material which is inert at the concentration level used (i.e., a material which has no reaction or limited reaction with the ink components) to facilitate the tagging compositions being incorporated into the inks to be tagged. The carrier may be a liquid in which one or more detectable markers may be dissolved to produce a substantially homogenous solution. Suitable liquids include, but are not limited to, solvents, water, and alcohols.

The tagging compositions of the present invention may be incorporated into an ink to produce a tagged ink having at least one detectable marker present in a detectable amount. As used herein, the term "authentic ink" refers to an ink which includes a detectable marker and which, accordingly, may comprise an artificial abundance of an isotope of an element which exceeds a natural amount of the isotope in the ink or an infrared fluorescing agent detectable with infrared light. By incorporating the detectable marker into an ink in this manner to produce an authentic ink, the quality and integrity of the ink may be preserved and yet the concentration of the detectable marker in the ink may be detected by suitable detection technology.

The tagged inks having the detectable marker are distributed in commerce such that the tagged inks may be purchased by consumers or retailers. In this manner, the ink vendor or manufacturer may test or authenticate their inks to reduce the incidence of ink counterfeiting or deter counterfeiters from producing counterfeit inks.

In one embodiment, the detection technology may comprise inductively coupled plasma mass spectrometry (ICP-MS), which is capable of detecting an isotope concentration for a number of different isotopes in the parts per billion (ppb) range in a relatively short period of time, (e.g., less than 10 minutes). In another embodiment, the detection technology may comprise a source of infrared light which may be used in combination with a separation means for separating the ink from the detectable marker.

In one embodiment, a method for tagging an ink for identification comprises incorporating a detectable marker into an ink. In one embodiment, the detectable marker may include an isotope that may be prepared or isolated for use in the tagging compositions using conventional isotope extraction methods, including plasma separation processes, electromagnetic separation, molecular laser isotope separation, atomic vapor laser isotope separation, gas centrifugation, gas diffusion, and distillation. Each of these methods is conventional and, accordingly, isotope extraction is not further discussed herein. Additionally, highly enriched samples of most stable isotopes are commercially available from a number of sources including, but not limited to, Inorganic Ventures/IV Labs of Lakewood, N.J.

In one embodiment, a method for tagging an ink for identification comprises tagging the ink with a detectable marker, such as, for example, a tagging composition comprising an augmented abundance of at least one isotope of an element or an infrared fluorescing agent to produce an authentic ink having an artificial abundance of at least one isotope of an element or the infrared fluorescing agent, which exceeds a natural abundance thereof in the authentic ink. At least one isotope may be present in the authentic ink in a concentration of from about 1 to about 1000 parts per billion.

In one embodiment, the tagging composition may comprise an augmented abundance of at least one isotope of a first element and at least one isotope of a second element. The first and second elements may be different from one another. An authentic ink including the tagging composition has an artificial abundance of at least one isotope of the first element and an artificial abundance of at least one isotope of the second element, each of which exceeds the respective natural abundances thereof in the authentic ink.

In another embodiment, the tagging composition may comprise an augmented abundance of at least two isotopes of a single element, wherein the artificial abundance of each of at least two isotopes exceeds a respective natural abundance thereof in the authentic ink. The tagging composition may have a ratio of the artificial abundance of a first of the at least two isotopes relative to the artificial abundance of a second of the at least two isotopes that is different from a natural abundance ratio for the isotopes in the authentic ink.

In a further embodiment, a method for authenticating an unidentified ink includes tagging an ink with a tagging composition having an augmented abundance of at least one isotope of an element or an infrared fluorescing agent to produce an authentic ink. The authentic ink may have an artificial abundance of at least one isotope or the infrared fluorescing agent which exceeds a natural abundance thereof in the authentic ink. A sample of the unidentified ink is obtained and an abundance of at least one isotope in the unidentified ink sample is detected using inductively coupled plasma mass spectrometry, or the infrared fluorescing agent is detected using an infrared light source to determine whether the unidentified ink is the authentic ink based upon a comparison of the detected abundance of at least one isotope in the unidentified ink sample and the artificial abundance of at least one isotope in the authentic ink sample, or based on the presence or the absence of the infrared fluorescing agent.

In one embodiment, if a ratio of the detected abundance of at least one isotope in the unidentified ink sample relative to the artificial abundance of at least one isotope in the authentic ink is less than 0.66, the unidentified ink may be designated as counterfeit. At least one isotope may be present in the composition in a concentration of between about 1 and about 1000 parts per billion and may be selected from isotopes of lithium, rubidium, cesium, certain alkaline metals (e.g., beryllium, magnesium, strontium, and barium), certain transition metals (e.g., manganese, cobalt, nickel, copper, zinc, yttrium, niobium, rhodium, and rhenium), certain rare earth elements (e.g., lanthanum, cerium, praseodymium, europium, gadolinium, terbium, and lutetium), and combinations of any thereof.

In yet another embodiment, a method for authenticating an ink includes obtaining a sample of an unidentified ink and detecting an abundance of at least one isotope of an element in the unidentified ink sample using inductively coupled plasma mass spectrometry or detecting the infrared fluorescing agent using an infrared light source. The detected abundance is compared to a tagging record which correlates an authentic ink identifier with information regarding an authentic ink. The authenticity of the unidentified ink is determined based upon a comparison of the detected abundance of at least one isotope or the presence of the infrared fluorescing agent in the unidentified ink sample and the tagging record. The authentic ink may comprise an artificial abundance of at least one isotope which exceeds a natural abundance of at least one isotope in the authentic ink or the infrared fluorescing agent. Additionally, at least one isotope may be present in the authentic ink in a concentration of between about 1 and about 1000 parts per billion and may be selected from isotopes of lithium, rubidium, cesium, certain alkaline metals (e.g., beryllium, magnesium, strontium, and barium), certain transition metals (e.g., manganese, cobalt, nickel, copper, zinc, yttrium, niobium, rhodium, and rhenium), certain rare earth elements (e.g., lanthanum, cerium, praseodymium, europium, gadolinium, terbium, and lutetium), and combinations of any thereof.

Any element having at least one stable isotope may be used in the tagging compositions of the present invention. In one embodiment, light elements are employed such as, for example, elements of the alkali group that tend to have limited interaction with the other components which typically are included in inkjet inks, as well as having limited interaction with the inkjet cartridge components.

By way of example, and not limitation, elements which may be used in one embodiment of the tagging compositions of the present invention include, but are not limited to lithium (Li), rubidium (Rb), cesium (Cs), certain alkaline metals (e.g., beryllium (Be), magnesium (Mg), strontium (Sr), and barium (Ba)), certain transition metals (e.g., manganese (Mn), cobalt (Co), nickel (Ni), copper (Cu), zinc (Zn), yttrium (Y), niobium (Nb), rhodium (Rh), and rhenium (Re)), and certain rare earth elements (e.g., lanthanum (La), cerium (Ce), praseodymium (Pr), europium (Eu), gadolinium (Gd), terbium (Tb), lutetium (Lu)), and any combinations thereof.

Each of the above listed exemplary elements has at least one stable isotope. In this regard, isotopes of the exemplary elements which are used in the tagging compositions of the present invention include, by way of example only and not limitation, $^6$Li, $^7$Li, $^{85}$Rb, $^{87}$Rb, $^{133}$Cs, $^9$Be, $^{24}$Mg, $^{25}$Mg, $^{26}$Mg, $^{84}$Sr, $^{86}$Sr, $^{87}$Sr, $^{88}$Sr, $^{130}$Ba, $^{132}$Ba, $^{134}$Ba, $^{135}$Ba, $^{136}$Ba, $^{137}$Ba, $^{138}$Ba, $^{55}$Mn, $^{59}$Co, $^{58}$Ni, $^{60}$Ni, $^{62}$Ni, $^{63}$Cu, $^{65}$Cu, $^{64}$Zn, $^{66}$Zn, $^{68}$Zn, $^{89}$Y, $^{93}$Nb, $^{103}$Rh, $^{185}$Re, $^{187}$Re, $^{139}$La, $^{140}$Ce, $^{141}$Pr, $^{151}$Eu, $^{153}$Eu, $^{152}$Gd, $^{154}$Gd, $^{155}$Gd, $^{157}$Gd, $^{160}$Gd, $^{159}$Tb, $^{175}$Lu, and any combinations thereof.

In one embodiment, the $^6$Li isotope is used as it is unique and highly sensitive to detection via ICP-MS in the shield plate cool plasma condition, i.e., it can be detected in a concentration as low as between about 1 and about 100 ppb. The element lithium (Li) has two stable isotopes with atomic masses of 6 and 7. In natural lithium, these two isotopes are present in the concentration of 7.50% and 92.50%, respectively. Accordingly, when an ink is tagged with the $^6$Li isotope, the abundance of the $^7$Li isotope is altered as well.

Combinations of isotopes and elements may be incorporated into the tagging compositions of the present invention to create authentic inks that are difficult for would-be counterfeiters to replicate.

In another embodiment, a method of the present invention includes incorporating a detectable marker into an ink. In one embodiment, the detectable marker may include an infrared fluorescing agent that may be detected under infrared (IR) light such as, for example, TINOLUX BBS.

In another embodiment, the present invention describes a method for authenticating an unidentified ink. When the detectable marker comprises at least one isotope, the method may comprise comparing information extracted from a sample of the unidentified ink with information that is known about an authentic ink and the one or more tagging compositions with which the authentic ink has been tagged, to determine whether the unidentified ink sample is a sample of the authentic ink or is a sample of a counterfeit ink.

In one embodiment, the method includes obtaining a sample of an unidentified ink and detecting an abundance in the unidentified ink sample of at least one isotope with which the authentic ink has been tagged using ICP-MS. The detected abundance of at least one isotope in the unidentified ink sample may subsequently be compared with the known artificial abundance of at least one isotope in the authentic ink to determine whether the unidentified ink sample is the authentic ink.

As the natural abundance of a given isotope in an ink is not constant, a simple comparison of the raw abundance numbers (i.e., isotope mass counts) may not provide an accurate indication of whether or not the two inks being compared are the same ink. Accordingly, in one embodiment, a ratio of the detected abundance of at least one isotope in the unidentified ink sample to the artificial abundance of at least one isotope in the authentic ink may be determined. If this ratio is less than about 0.66, the unidentified ink sample may be designated as counterfeit. However, if this ratio is greater than or equal to 0.66, it is likely that the unidentified ink sample is a sample of the authentic ink.

In one embodiment, an ink may be tagged with a tagging composition comprising an augmented abundance of at least one isotope of a first element and an augmented abundance of at least one isotope of a second element, the first and second elements being different from one another, to produce the authentic ink. If a tagging composition in accordance with this embodiment is utilized to produce the authentic ink, an abundance of each of two isotopes may be detected in the unidentified ink sample and that information regarding the artificial abundances of the two isotopes be known with respect to the authentic ink. Using this information, a ratio of the detected abundance of the isotope of a first element in the unidentified ink sample to the artificial abundance of the isotope of the first element in the authentic ink may be determined, as may a ratio of the detected abundance of the isotope of a second element in the unidentified ink sample to the artificial abundance of the isotope of the second element in the authentic ink. If either or both of these ratios are less than 0.66, the unidentified ink sample may be designated as counterfeit.

An unidentified isotope ratio may be determined for the unidentified ink sample. The unidentified isotope ratio is a ratio of the detected abundance of at least one isotope of the first element to the detected abundance of at least one isotope of the second element in the unidentified ink sample. Similarly, an authentic isotope ratio, i.e., the ratio of the artificial abundance of at least one isotope of the first element to the artificial abundance of at least one isotope of the second element in the authentic ink sample, may be determined. If the ratio of the unidentified isotope ratio to the authentic isotope ratio is less than 0.66, the unidentified ink sample may be designated as counterfeit.

Further, in another embodiment, an ink may be tagged with a tagging composition comprising an augmented abundance of at least two isotopes of a single element to produce an authentic ink. If a tagging composition in accordance with this embodiment is utilized to produce the authentic ink, an abundance of each of at least two isotopes of the element may be detected in the unidentified ink sample and that information regarding the artificial abundance of each of at least two isotopes of the element be known with respect to the authentic ink. An unidentified isotope ratio, (i.e., the ratio of the detected abundance of a first of the at least two isotopes of the element to the detected abundance of a second of at least two isotopes of the element) may be determined for the unidentified ink sample and that an authentic isotope ratio (i.e., the ratio of the artificial abundance of a first of at least two isotopes of the element to the artificial abundance of a second of the at least two isotopes of the element) be determined for the authentic ink.

Using this information, a ratio of the detected abundance of a first of at least two isotopes of the element in the unidentified ink sample to the artificial abundance of the first of at least two isotopes of the element in the authentic ink may be determined, as may a ratio of the detected abundance of the second of at least two isotopes of the element in the unidentified ink sample to the artificial abundance of the second of at least two isotopes of the element in the authentic ink. If either or both of these ratios are less than 0.66, the unidentified ink sample may be designated as counterfeit. Further, if the ratio of the unidentified isotope ratio to the authentic isotope ratio is less than 0.66, the unidentified ink sample may also be designated as counterfeit.

To facilitate a comparison between information extracted from an unidentified ink sample and information known about an authentic ink, information regarding the authentic ink may be recorded in a tagging record for use in determining authenticity and detecting counterfeit inks. The term "tagging record," as used herein, refers to information (record) which correlates an identifier for the authentic ink with information regarding the detectable marker with which the ink has been tagged. For instance, an authentic ink identifier may comprise one or more pieces of information about the ink including, but not limited to, a serial number, a batch number, a lot number the date of manufacture, and the name brand of the ink. The authentic ink identifier may be correlated in the tagging record with information regarding the isotope(s), the infrared fluorescing agent, or a combination thereof with which the ink has been tagged, including, but not limited to, the element used for tagging, the isotope of the element that was used (if there is more than one stable isotope), the concentration at which the isotope is present in the ink, the type of infrared fluorescing agent in the ink, the wavelength of light at which the infrared fluorescing agent fluoresces in the ink, and which inks in a cartridge the detectable marker is placed. Tagging records may be made at the time an authentic ink is tagged.

In an additional embodiment, a tagging record may include information about which inks or dyes in an ink set include an isotope(s) and an infrared fluorescing agent. In this manner, a presumptive, qualitative test may be performed on an ink sample in the field to determine whether the infrared fluorescing agent is present in the ink. If the qualitative test indicates that the infrared fluorescing agent is present in the ink, a quantitative test may be performed to quantitate the amount of isotope(s) present in the ink and further characterize the ink sample to determine if the ink sample is authentic.

In another embodiment, the detectable marker may include an infrared fluorescing agent that is detectable with infrared light. A method for authenticating an unidentified ink includes subjecting the unidentified ink to a process capable of separating the detectable marker from the ink components of the unidentified ink, and subjecting the separated ink components to a source of infrared illumination such that, if present, the separated detectable marker will be illuminated with the infrared light.

In a further embodiment, a system for identifying an unidentified ink includes a separation means for separating a detectable marker, if present, from components of an ink. The system also includes a light source for producing infrared light and an infrared viewer for detecting any fluorescence generated by the detectable marker if present in the unidentified ink. The separation means may comprises a solvent and use of a chromatograph as described herein. The infrared viewer may be a single chip black and white camera. In another embodiment, the system is configured to be portable such that the system may be utilized in the field such as, for example, at a retail store.

The following examples describe various embodiments of methods and systems for authenticating an ink in accordance with the present invention. The examples are merely illustrative and are not meant to limit the scope of the present invention in any way.

Example 1

Preparation of an Authentic Ink

An isotope solution enriched with the $^6$Li isotope was obtained from Inorganic Ventures/IV Labs of Lakewood, N.J. The $^6$Li isotope enriched solution contained about 1002±1 ppm $^6$Li and 67±1 ppm $^7$Li in 5.0% $HNO_3$. Thus, it can be seen that the $^6$Li isotope enriched solution contained about 6.7% $^7$Li isotope as well. A 5 part per million (ppm) $^6$Li isotope stock solution was prepared from the $^6$Li enriched isotope solution by diluting the $^6$Li enriched isotope solution with deionized water. A tagged ink having a detectable marker was prepared from the $^6$Li isotope stock solution by adding 0.1 g of the $^6$Li isotope stock solution to 50 g of ink. The resulting ink was a 10 ppb $^6$Li isotope tagged ink which was labeled as the "authentic" ink.

A sample of the authentic ink was diluted 100 fold with deionized water. The diluted samples were introduced into an Agilent-4500 Inductively Coupled Plasma Mass Spectrometry (ICP-MS) instrument, obtained from Agilent Technologies of Palo Alto, Calif. and the cool plasma method was used to measure the isotope mass counts. The ICP-MS instrumentation and the cool plasma method are well known to those of ordinary skill in the art and, accordingly, are not discussed further herein. Cobalt (Co) was added as the internal standard to compensate for any instrument drift and sample matrix effect. The instrument was not tuned to optimize the detection of light masses.

$^6$Li isotope and $^7$Li isotope mass counts, as well as the ratio of $^6$Li:$^7$Li are shown in each of FIGS. 1-5 for the authentic ink. The authentic ink is labeled as 10 ppb $^6$Li Tagged Ink.

A number of different inks were tagged in this manner and are labeled as ink samples A-E in FIGS. 1-5. Ink sample A was a black ink, ink sample B was a magenta ink, ink sample C was a yellow ink, ink sample D was a cyan ink having a first formulation, and ink sample E was a cyan ink having a second formulation. Each of the ink samples was prepared for purposes of the experiments at the San Diego, Calif. facility of Hewlett-Packard Company. Additionally, a number of the below-described experiments were run at two separate times. Accordingly, each of ink samples A-E is also labeled as 1 and 2 to indicate two different runs.

Example 2

Preparation of 20% Adulterated Ink

An ink adulterated by 20% relative to the authentic ink was prepared by mixing a sample of the authentic ink with an untagged ink of the same type and color to obtain an 8 ppb $^6$Li adulterated ink. Samples of the 20% adulterated ink were diluted 100 fold with deionized water. The diluted samples were introduced into the Agilent-4500 ICP-MS instrument and the cool plasma method was used to measure the isotope mass counts. As with the authentic ink samples, cobalt (Co) was added as the internal standard to compensate for any instrument drift and sample matrix effect and the instrument was not tuned to optimize the detection of light masses.

The $^6$Li and $^7$Li mass counts, as well as the ratio of $^6$Li:$^7$Li are shown in FIG. 1. The 20% adulterated ink is labeled as 8 ppb $^6$Li Ink.

In a first comparison, using the $^6$Li mass counts of the authentic ink and the 20% adulterated ink, the ratio of the $^6$Li mass count of the adulterated ink to the $^6$Li mass count of the authentic ink was determined. These values are shown for each ink sample in FIG. 1 under the heading $^6$Li Counts Adulterated/Authentic.

If the ratio of the $^6$Li mass count of the adulterated ink to the $^6$Li mass count of the authentic ink was greater than 0.66, the ink sample was indicated as "Authentic." If, however, the ratio of the $^6$Li mass count of the adulterated ink to the $^6$Li mass count of the authentic ink was less than or equal to 0.66, the ink sample was indicated as "Fake 1." As shown in FIG. 1, each of samples A1, A2, B1, B2, C2, D1, D2, E1, and E2 was indicated as Authentic and sample C1 was indicated as "Fake 1."

In a second comparison, using the $^6$Li:$^7$Li ratios for both the authentic ink and the 20% adulterated ink, the ratio of the $^6$Li:$^7$Li ratio of the adulterated ink to the $^6$Li:$^7$Li ratio of the authentic ink was determined. These values are also shown for each ink sample in FIG. 1 under the heading $^6$Li/$^7$Li Ratios Adulterated/Authentic.

If the $^6$Li:$^7$Li ratio of the adulterated ink to the $^6$Li:$^7$Li ratio of the authentic ink was greater than 0.66, the ink sample was indicated as "Authentic." If, however, the $^6$Li:$^7$Li ratio of the authentic ink was less than or equal to 0.66, the ink sample was indicated as "Fake 2." As shown in FIG. 1, each of samples A1, A2, B1, B2, C2, D1, D2, E1, and E2 was indicated as "Fake 2" and ink sample C1 was indicated as "Authentic."

If either of the first or second comparisons yielded an ink that was indicated as fake (i.e., either "Fake 1" or "Fake 2"), the ink was designated as counterfeit. As such, at only 20% adulteration, the methods of the present invention identified each of the ink samples as counterfeit.

Example 3

Preparation of 50% Adulterated Ink

An ink adulterated by 50% relative to the authentic ink was prepared by mixing a sample of the authentic ink with an untagged ink of the same type and color to obtain a 5 ppb $^6$Li adulterated ink. Samples of the 50% adulterated ink were diluted 100 fold with deionized water. The diluted samples were introduced into the Agilent-4500 ICP-MS instrument and the cool plasma method was used to measure the isotope mass counts. As with the authentic ink samples, cobalt (Co) was added as the internal standard to compensate for any instrument drift and sample matrix effect and the instrument was not tuned to optimize the detection of light masses.

The $^6$Li and $^7$Li mass counts, as well as the ratio of $^6$Li:$^7$Li are shown in FIG. 2. The 50% adulterated ink is labeled as 5 ppb $^6$Li Ink.

In a first comparison, using the $^6$Li mass counts of both the authentic ink and the 50% adulterated ink, the ratio of the $^6$Li mass count of the adulterated ink to the $^6$Li mass count of the authentic ink was determined. These values are shown for each ink sample in FIG. 2 under the heading $^6$Li Counts Adulterated/Authentic.

If the ratio of the $^6$Li mass count of the adulterated ink to the $^6$Li mass count of the authentic ink was greater than 0.66, the ink sample was indicated as "Authentic." If, however, the ratio of the $^6$Li mass count of the adulterated ink to the $^6$Li mass count of the authentic ink was less than or equal to 0.66, the ink sample was indicated as "Fake 1." As shown in FIG. 2, each of the ink samples was indicated as "Fake 1."

In a second comparison, using the $^6$Li:$^7$Li ratios for both the authentic ink and the 50% adulterated ink, the ratio of the $^6$Li:$^7$Li ratio of the adulterated ink to the $^6$Li:$^7$Li ratio of the authentic ink was determined. These values are also shown for each ink sample in FIG. 2 under the heading $^6$Li/$^7$Li Ratios Adulterated/Authentic.

If the $^6$Li:$^7$Li ratio of the adulterated ink to the $^6$Li:$^7$Li ratio of the authentic ink was greater than 0.66, the ink sample was indicated as "Authentic." If, however, the $^6$Li:$^7$Li ratio of the authentic ink was less than or equal to 0.66, the ink sample was indicated as "Fake 2." As shown in FIG. 2, each of the ink samples in this experiment was indicated as "Fake 2."

If either of the first or second comparisons yielded an ink that was indicated as fake (i.e., either "Fake 1" or "Fake 2"), the ink was designated as counterfeit. As such, at 50% adulteration, the methods of the present invention identified each of the ink samples as counterfeit.

Example 4

Preparation of 80% Adulterated Ink

An ink adulterated by 80% relative to the authentic ink was prepared by mixing a sample of the authentic ink with an untagged ink of the same type and color to obtain an 2 ppb $^6$Li adulterated ink. Samples of the 80% adulterated ink were diluted 100 fold with deionized water. The diluted samples were introduced into the Agilent-4500 ICP-MS instrument and the cool plasma method was used to measure the isotope mass counts. As with the authentic ink samples, cobalt (Co) was added as the internal standard to compensate for any instrument drift and sample matrix effect and the instrument was not tuned to optimize the detection of light masses.

The $^6$Li and $^7$Li mass counts, as well as the ratio of $^6$Li:$^7$Li are shown in FIG. 3. The 80% adulterated ink is labeled as 2 ppb $^6$Li Ink.

In a first comparison, using the $^6$Li mass counts of the authentic ink and the 80% adulterated ink, the ratio of the $^6$Li mass count of the adulterated ink to the $^6$Li mass count of the authentic ink was determined. These values are shown for each ink sample in FIG. 3 under the heading $^6$Li Counts Adulterated/Authentic.

If the ratio of the $^6$Li mass count of the adulterated ink to the $^6$Li mass count of the authentic ink was greater than 0.66, the ink sample was indicated as "Authentic." If, however, the ratio of the $^6$Li mass count of the adulterated ink to the $^6$Li mass count of the authentic ink was less than or equal to 0.66, the ink sample was indicated as "Fake 1." As shown in FIG. 3, each of the ink samples was indicated as "Fake 1."

In a second comparison, using the $^6$Li:$^7$Li ratios for both the authentic ink and the 80% adulterated ink, the ratio of the $^6$Li:$^7$Li ratio of the adulterated ink to the $^6$Li:$^7$Li ratio of the authentic ink was determined. These values are also shown for each ink sample in FIG. 3 under the heading $^6$Li/$^7$Li Ratios Adulterated/Authentic.

If the $^6$Li:$^7$Li ratio of the adulterated ink to the $^6$Li:$^7$Li ratio of the authentic ink was greater than 0.66, the ink sample was indicated as "Authentic." If, however, the $^6$Li:$^7$Li ratio of the authentic ink was less than or equal to 0.66, the ink sample was indicated as "Fake 2." As shown in FIG. 3, each of the ink samples was indicated as "Fake 2."

If either of the first or second comparisons yielded an ink that was indicated as fake (i.e., either "Fake 1" or "Fake 2"), the ink was designated as counterfeit. As such, at 80% adulteration, the methods of the present invention identified each of the ink samples as counterfeit.

Example 5

Preparation 50% Diluted Ink

An ink diluted by 50% relative to the authentic ink with deionized water was prepared to obtain an 5 ppb $^6$Li diluted ink. The 50% diluted ink sample was diluted 100 fold with deionized water. The diluted sample was introduced into the Agilent-4500 ICP-MS instrument and the cool plasma method was used to measure the isotope mass counts. As with the authentic ink samples, cobalt (Co) was added as the internal standard to compensate for any instrument drift and sample matrix effect and the instrument was not tuned to optimize the detection of light masses.

The $^6$Li and $^7$Li mass counts, as well as the ratio of $^6$Li:$^7$Li are shown in FIG. 4. The 50% diluted ink is labeled as 5 ppb $^6$Li Ink.

In a first comparison, using the $^6$Li mass counts of both the authentic ink and the 50% diluted ink, the ratio of the $^6$Li mass count of the adulterated ink to the $^6$Li mass count of the authentic ink was determined. These values are shown for each ink sample in FIG. 4 under the heading $^6$Li Counts Adulterated/Authentic.

If the ratio of the $^6$Li mass count of the adulterated ink to the $^6$Li mass count of the authentic ink was greater than 0.66, the ink sample was indicated as "Authentic." If, however, the ratio of the $^6$Li mass count of the adulterated ink to the $^6$Li mass count of the authentic ink was less than or equal to 0.66, the ink sample was indicated as "Fake 1." As shown in FIG. 4, each of samples A2, B2 and D2 was indicated as "Fake 1" and each of samples C2 and E2 was indicated as "Authentic."

In a second comparison, using the $^6$Li:$^7$Li ratios for both the authentic ink and the 50% diluted ink, the ratio of the $^6$Li:$^7$Li ratio of the adulterated ink to the $^6$Li:$^7$Li ratio of the authentic ink was determined. These values are also shown for each ink sample in FIG. 4 under the heading $^6$Li/$^7$Li Ratios Adulterated/Authentic.

If the $^6$Li:$^7$Li ratio of the adulterated ink to the $^6$Li:$^7$Li ratio of the authentic ink was greater than 0.66, the ink sample was indicated as "Authentic." If, however, the $^6$Li:$^7$Li ratio of the authentic ink was less than or equal to 0.66, the ink sample was indicated as "Fake 2." As shown in FIG. 4, each of samples A2, C2, and D2 was indicated as "Authentic" and each of samples B2 and E2 was indicated as "Fake 2."

If either of the first or second comparisons yielded an ink that was indicated as fake (i.e., either "Fake 1" or "Fake 2"), the ink was designated as counterfeit. As such, at 50% dilution, the methods of the present invention identified four out of the five ink samples as counterfeit. Ink sample C2 was indicated as "Authentic" in both comparisons indicating possible contamination or detection error.

Example 6

Preparation of 80% Diluted Ink

An ink diluted by 80% relative to the authentic ink with deionized water was prepared to obtain an 2 ppb $^6$Li diluted ink. The 80% diluted ink sample was further diluted 100 fold with deionized water. The diluted sample was introduced into the Agilent-4500 ICP-MS instrument and the cool plasma method was used to measure the isotope mass counts. As with the authentic ink samples, cobalt (Co) was added as the internal standard to compensate for any instrument drift and sample matrix effect and the instrument was not tuned to optimize the detection of light masses.

The $^6$Li and $^7$Li mass counts, as well as the ratio of $^6$Li:$^7$Li are shown in FIG. 5. The 80% diluted ink is labeled as 2 ppb $^6$Li Ink.

In a first comparison, using the $^6$Li mass counts of both the authentic ink and the 80% diluted ink, the ratio of the $^6$Li mass count of the adulterated ink to the $^6$Li mass count of the authentic ink was determined. These values are shown for each ink sample in FIG. 5 under the heading $^6$Li Counts Adulterated/Authentic.

If the ratio of the $^6$Li mass count of the adulterated ink to the $^6$Li mass count of the authentic ink was greater than 0.66, the ink sample was indicated as "Authentic." If, however, the ratio of the $^6$Li mass count of the adulterated ink to the $^6$Li mass count of the authentic ink was less than or equal to 0.66, the ink sample was indicated as "Fake 1." As shown in FIG. 5, each of the ink samples was indicated as "Fake 1."

In a second comparison, using the $^6$Li:$^7$Li ratios for both the authentic ink and the 80% diluted ink, the ratio of the $^6$Li:$^7$Li ratio of the adulterated ink to the $^6$Li:$^7$Li ratio of the authentic ink was determined. These values are also shown for each ink sample in FIG. 5 under the heading $^6$Li/$^7$Li Ratios Adulterated/Authentic.

If the $^6$Li:$^7$Li ratio of the adulterated ink to the $^6$Li:$^7$Li ratio of the authentic ink was greater than 0.66, the ink sample was indicated as "Authentic." If, however, the $^6$Li:$^7$Li ratio of the authentic ink was less than or equal to 0.66, the ink sample was indicated as "Fake 2." As shown in FIG. 5, each of samples B2, D2, and E2 was indicated as "Fake 2" and each of ink samples A2 and C2 was indicated as "Authentic."

If either of the first or second comparisons yielded an ink that was indicated as fake (i.e., either "Fake 1" or "Fake 2"), the ink was designated as counterfeit. As such, at 80% dilution, the methods of the present invention identified each of the ink samples as counterfeit.

Example 7

In one embodiment, a detectable marker such as, for example, an infrared fluorescing agent capable of fluorescing when exposed to infrared (IR) light, is added to ink such as, for example, ink for a thermal ink jet printer such that the presence or absence of the detectable marker may be assayed. The detectable marker is selected such that the detectable marker does not interfere with ink performance, is not visible under normal conditions (i.e., visible to the naked eye under normal or white light) and does not cause failure of a device (i.e., a nozzle of an ink jet print head used to place the ink on a substrate).

Referring now to FIG. 6, there is shown a molecular diagram of one embodiment of a detectable marker 100 which may be employed in the present invention. In one embodiment, the detectable marker comprises an infrared fluorescing agent such as, for example, TINOLUX BBS. In other embodiments, the detectable marker may comprise any other detectable marker capable of fluorescing when exposed to infrared (IR) light such as for example, metal phthalocyanines including zinc, cadmium, tin, magnesium, europium, aluminum, and combinations of any thereof. In yet another embodiment, the detectable marker may comprise 1,1',3,3,3', 3'-hexamethylindotricarbocyanines or 1,1',3,3,3',3'-hexamethylindodicarbocyanines.

The ink to which the detectable marker is added may comprise one of the inks conventionally used in an ink jet printer (i.e., yellow (Y), magenta (M), cyan (C), black (K), a transparent ink, or combinations of any thereof). In other embodiments, the detectable marker may be added to other substances used in the printing industry, such as, for example, fixer, clear ink, or an optimizing solution, and may be added to inks used in any type of printer.

In one embodiment, the TINOLUX BBS was added to transparent ink, yellow ink, magenta ink, cyan ink, and black ink designed for use in an HP DesignJet 5500 printer. As conventionally known, the colored inks (i.e., yellow ink, magenta ink, cyan ink, and black ink) each include at least one colorant that is visible under visible light and that imparts color to the ink. The TINOLUX BBS was added at a concentration of about 50 ppm (parts per million). In other embodiments, the TINOLUX BBS or other infrared fluorescing agent may be added to the ink at a concentration of between about 10 ppm and about 10000 ppm. The concentration of the infrared fluorescing agent in the ink should be such that the infrared fluorescing agent is detectable, but does not affect the print quality of the ink.

Example 8

In another embodiment, a method of testing an unidentified ink for authenticity includes subjecting the unidentified ink to a separation procedure such as, for example, thin layer chromatography, and subjecting the separated ink to infrared light. The separation procedure separates any colorant (i.e., dye or pigment) in the ink from the detectable marker such that the detectable marker may be detected. In this manner, if the ink includes an infrared fluorescing agent as the detectable marker, the infrared fluorescing agent will fluoresce when subjected to infrared light, thus, indicating that the ink is authentic. If the ink does not include the infrared fluorescing agent, the ink may be deemed to be non-authentic.

In other embodiments, the separation procedure may include other conventional chromatography procedures such as, for example, liquid chromatography. In a further embodiment, the separation procedure may include placing the ink on a separation material, such as a filter, or other conventional separation procedures.

In an additional embodiment, the separation procedure may be omitted and the ink, including the detectable marker, may be subjected to the infrared light. This embodiment is applicable to inks or substances that do not include a colorant (e.g., transparent ink or fixer) or includes a colorant that does not prevent the detectable marker from being seen (e.g., yellow ink or magenta ink) when subjected to the infrared light.

In one embodiment, the transparent ink and colorant-based inks including yellow ink, magenta ink, cyan ink, and black ink were prepared, wherein each ink included the infrared fluorescing agent TINOLUX BBS at a concentration of about 50 ppm. Each of the transparent ink, the yellow ink, the magenta ink, the cyan ink, and the black ink were placed on a reverse phase Thin Layer Chromatography Plate such as, for example, a TLC Whatman, KC 18. A solvent such as, for example, methanol/water was used as a mobile phase to separate the TINOLUX BBS from the components of the transparent ink, yellow ink, magenta ink, cyan ink, and black ink, wherein the separation Rf was selected to be about from about 0.2 to about 0.9.

In other embodiments, the solvent may comprise acetonitrile, dichloromethane (DCM), hexane, acetone, other alcohol solvents, such as, for example, ethanol or propanol, or any combinations thereof, wherein the concentration of the solvent is from about 20% to about 95% in a normal separation. Other types of Thin Layer Chromatographies (TLC) that may be used to separate the infrared fluorescing agent from the ink ingredients or components include, but are not limited to, cellulose, aluminum oxide, silica gel, polyamide normal phase TLC, or C-8, C-18 reversed phrase TLC.

Figure 7:
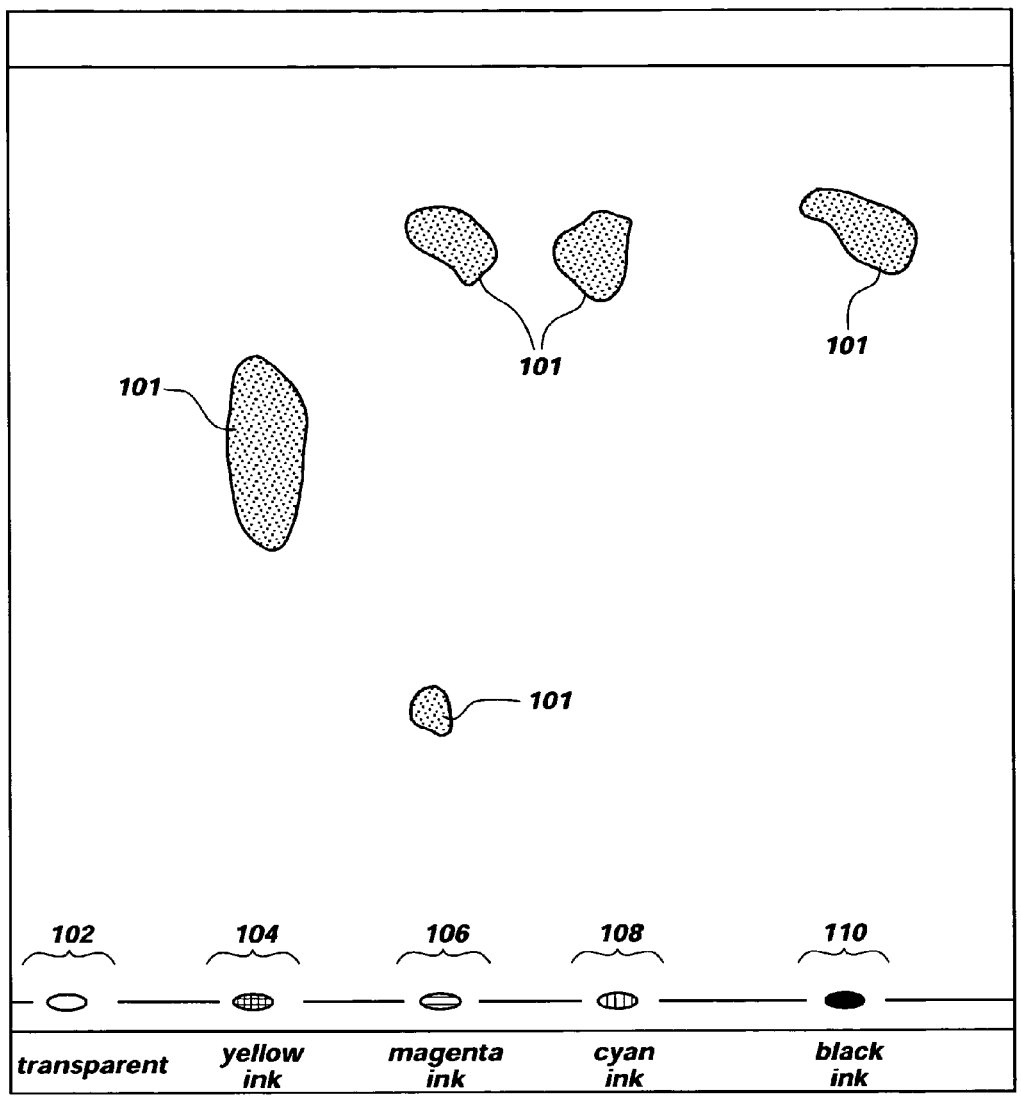
FIG. 7 illustrates the results of one embodiment of a method of separating ink from the infrared marker of the present invention when viewed under visible light.

Ink components 101 of each of the transparent ink, the yellow ink, the magenta ink, the cyan ink, and the black ink were separated, as shown in the patterns of FIG. 7, when illuminated with visible light, such as, white light. The transparent ink was separated in lane 102, the yellow ink was separated in lane 104, the magenta ink was separated in lane 106, the cyan ink was separated in lane 108, and the black ink was separated in lane 110.

Figure 8:
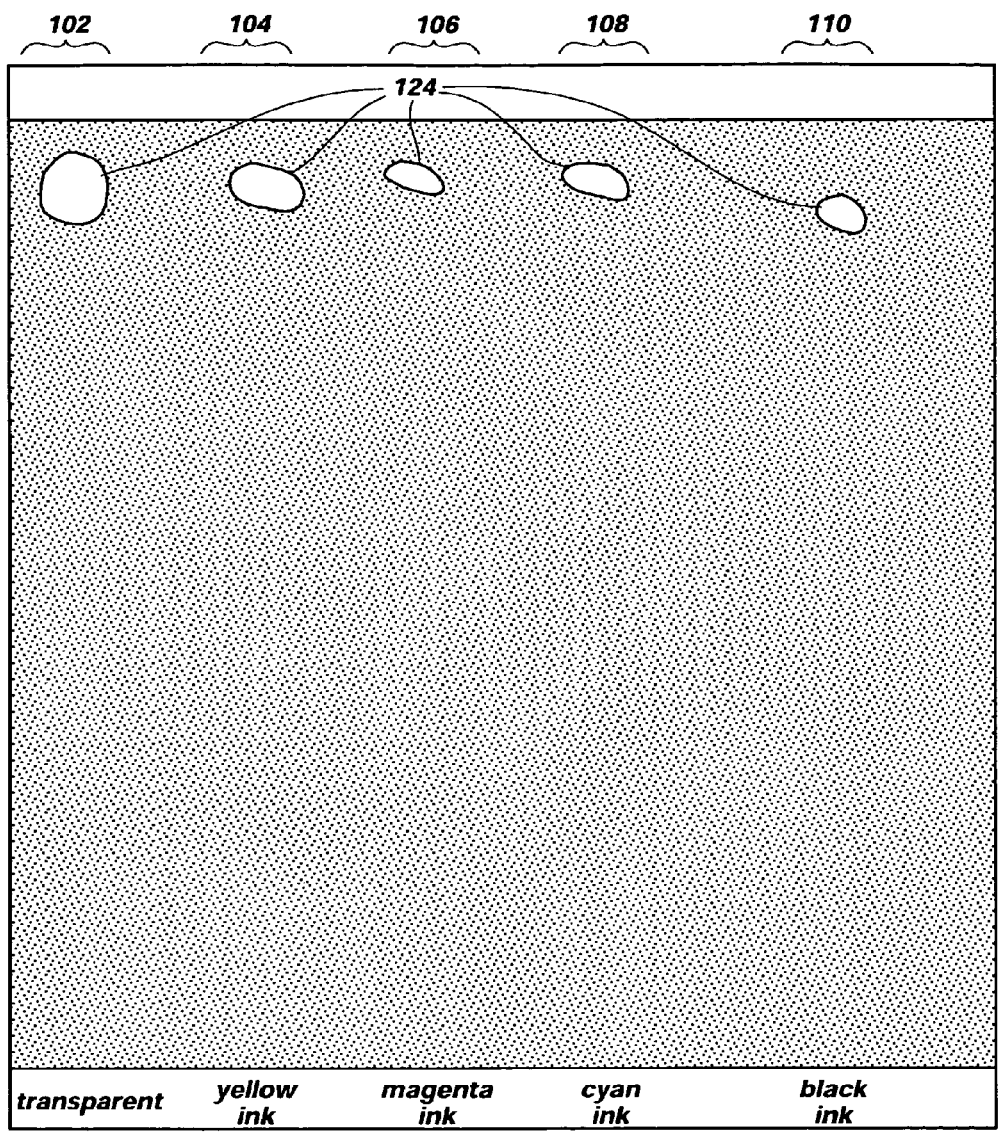
FIG. 8 illustrates the results of the method of separating ink from the infrared marker as shown in FIG. 7 under infrared light.

The separated inks in each of lanes 102, 104, 106, 108, and 110 were subjected to infrared light and viewed with an infrared viewer, as illustrated in FIG. 8. A fluorescent area 124 in each of the lanes 102, 104, 106, 108, and 110 represents the TINOLUX BBS which is visible when subjected to the infrared light source and viewed with the infrared viewer.

In one embodiment, the infrared viewer comprises a single chip black and white camera with an infrared blocking viewer of the camera removed. The specifications of the single chip black and white camera used in this embodiment are as follows: a center wavelength of about 710 nm (nominal), wherein ≤0.01% T is blocked at about 400 nm to 650 nm and at about 775 nm to 1200 nm. The specifications of the infrared light source used in this embodiment are as follows: a center wavelength of about 649 nm (nominal), wherein at least 60% of the light is transmitted and 0.01% T is blocked at about 400 nm to 600 nm and at about 700 nm to about 1000 nm.

Example 9

In a further embodiment, the infrared fluorescing agent may be mixed with an ink having a pigment or the colorant to produce an authentic ink. In this embodiment, the method for testing the unidentified ink for authenticity includes subjecting the unidentified ink to a separation procedure such as, for example, Thin Layer Chromatography, and subjecting the separated ink to infrared light. The separation procedure separates any pigments in the unidentified ink from the detectable marker such that the detectable marker may be detected. In this manner, if the ink includes an infrared fluorescing agent as the detectable marker, the infrared fluorescing agent will fluoresce when subjected to infrared light and indicate that the ink is authentic. If the ink does not include the infrared fluorescing agent, the ink may be deemed to be non-authentic.

In one embodiment, TINOLUX BBS was added to dark cyan and light cyan pigmented inks at a concentration of about 100 ppm. The pigmented inks including the TINOLUX BBS were subjected to Thin Layer Chromatography (i.e., a C-18 reverse phase, using 70% MeOH as the solvent). The separated pigmented inks were viewed with visible light, as illustrated in FIG. 9A, where dark cyan was run in lane 120 and light cyan was run in lane 122. FIG. 9B illustrates the separated inks of FIG. 9A viewed under infrared light. The location of the TINOLUX BBS in the two lanes is illustrated at light areas 124.

Example 10

A system of authenticating an unidentified ink includes a separation means for separating components of the unidentified ink from the detectable marker, an infrared light source for subjecting the separated unidentified ink or the unidentified ink to infrared light, and an infrared viewer for causing the detectable marker to fluoresce, if present, under infrared light. The system may be configured to be mobile (i.e., portable) such that the system may be used in the field to authenticate or detect unidentified inks. In this manner, an ink jet technician may take an ink sample from an ink cartridge at a store and subject the ink sample to testing to see if the ink is authentic (i.e., whether the ink includes the detectable marker in the proportions placed in the ink when the ink is manufactured).

By employing the inks including detectable markers, methods and systems described herein, an ink manufacturer or vendor may distribute the authentic inks in commerce and test inks to ensure that the inks are authentic. In this manner, the manufacturer or vendor may reduce the incidence of counterfeiting or deter counterfeiters from trying to replicate the authentic ink produced by the manufacturer or sold by the vendor.

Although the present invention has been shown and described with respect to various exemplary embodiments, various additions, deletions, and modifications that are obvious to a person of ordinary skill in the art to which the invention pertains, even if not shown or specifically described herein, are deemed to lie within the scope of the invention as encompassed by the following claims. Further, features or elements of different embodiments may be employed in combination.

What is claimed is:

1. An ink composition, comprising:
a colorant visible under visible light; and
a tagging composition, including:
    a carrier; and
    a detectable marker dispersed or dissolved in the carrier, the detectable marker being an isotope of an element, the isotope being present in the ink composition in a concentration ranging from about 1 parts per billion (ppb) to about 1000 ppb.

2. The ink composition as defined in claim 1 wherein the isotope of the element is selected from the group consisting of isotopes of lithium, rubidium, cesium, beryllium, magnesium, strontium, barium, manganese, cobalt, nickel, copper, zinc, yttrium, niobium, rhodium, rhenium, and combinations thereof.

3. The ink composition as defined in claim 1 wherein the detectable marker includes a $^6$Li isotope and a $^7$Li isotope, and wherein a mass count ratio of $^6$Li isotope:$^7$Li isotope present in the ink composition ranges from 1.50 to 13.73.

4. The ink composition as defined in claim 1 wherein the colorant is black, magenta, yellow, or cyan.

5. The ink composition as defined in claim 1 wherein the isotope of the element is selected from the group consisting of $^6$Li, $^7$Li, $^{85}$Rb, $^{87}$Rb, $^{133}$Cs, $^9$Be, $^{24}$Mg, $^{25}$Mg, $^{26}$Mg, $^{84}$Sr, $^{86}$Sr, $^{87}$Sr, $^{88}$Sr, $^{130}$Ba, $^{132}$Ba, $^{134}$Ba, $^{135}$Ba, $^{136}$Ba, $^{137}$Ba, $^{138}$Ba, $^{55}$Mn, $^{59}$Co, $^{58}$Ni, $^{60}$Ni, $^{62}$Ni, $^{63}$Cu, $^{65}$Cu, $^{64}$Zn, $^{66}$Zn, $^{68}$Zn, $^{89}$Y, $^{93}$Nb, $^{103}$Rh, $^{185}$Re, $^{187}$Re, $^{139}$La, $^{140}$Ce, $^{141}$Pr, $^{151}$Eu, $^{153}$Eu, $^{152}$Gd, $^{154}$Gd, $^{155}$Gd, $^{157}$Gd, $^{160}$Gd, $^{159}$Tb, $^{175}$Lu, and combinations thereof.

* * * * *

UNITED STATES PATENT AND TRADEMARK OFFICE
CERTIFICATE OF CORRECTION

PATENT NO. : 8,669,536 B2  Page 1 of 1
APPLICATION NO. : 13/765131
DATED : March 11, 2014
INVENTOR(S) : Zeying Ma et al.

It is certified that error appears in the above-identified patent and that said Letters Patent is hereby corrected as shown below:

On the Title page, in item (71), Applicant, in column 1, line 1, delete "Developement" and insert -- Development --, therefor.

Signed and Sealed this
Fifteenth Day of July, 2014

Michelle K. Lee
*Deputy Director of the United States Patent and Trademark Office*